United States Patent [19]

Bringhurst et al.

[11] Patent Number: Plant 7,614

[45] Date of Patent: Aug. 6, 1991

[54] STRAWBERRY PLANT NAMED 'SEASCAPE'

[75] Inventors: Royce S. Bringhurst, Davis; Victor Voth, Santa Ana, both of Calif.

[73] Assignee: The Regents of the University of California, Berkeley, Calif.

[21] Appl. No.: 479,499

[22] Filed: Feb. 13, 1990

[51] Int. Cl.[5] ..... A01H 5/08

[52] U.S. Cl. ..... Plt./49

[58] Field of Search ..... Plt./48, 49

*Primary Examiner*—James R. Feyrer

*Attorney, Agent, or Firm*—Townsend and Townsend

[57] ABSTRACT

'Seascape' is a day-neutral type strawberry variety similar to 'Selva' but with a somewhat lower chilling requirement. It is noteworthy for high flavor, high yield, large fruit size, firmness, symmetry, attractive appearance and general flexibility in planting requirements.

2 Drawing Sheets

DESCRIPTION

This invention relates to a new and distinctive day-neutral type strawberry cultivar designated as 'Seascape' which is the result of a cross between 'Selva' (U.S. Plant Pat. No. 5,266)×'Douglas' (U.S. Plant Pat. No. 4,487), made in 1983.

'Seascape' first fruited at the University of California Wolfskill Experimental Orchards near Davis, Calif. in 1984, where it was selected and designated originally as Cal 83.49-1. It was tested later as advanced selection CN 49.

'Seascape' has been propagated asexually by runners and has been tested at various University of California field stations and research facilities and to a very limited extent in a few growers' fields under Test Agreement.

In the photographs:

Figure 1:
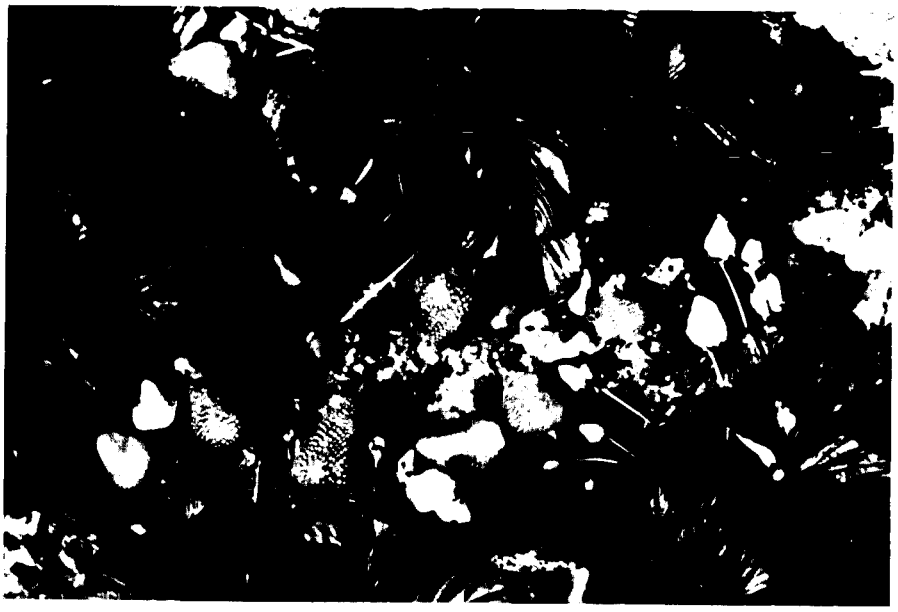
FIG. 1 shows typical growth, flowering and fruiting characteristics of the plant.
Figure 2:
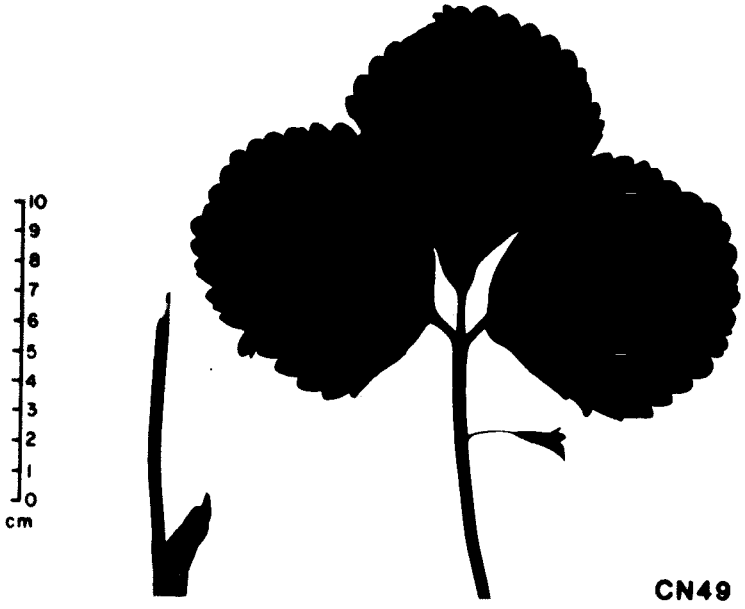
FIG. 2 shows a typical midsummer mature leaf from a plant in full fruit.
Figure 3:
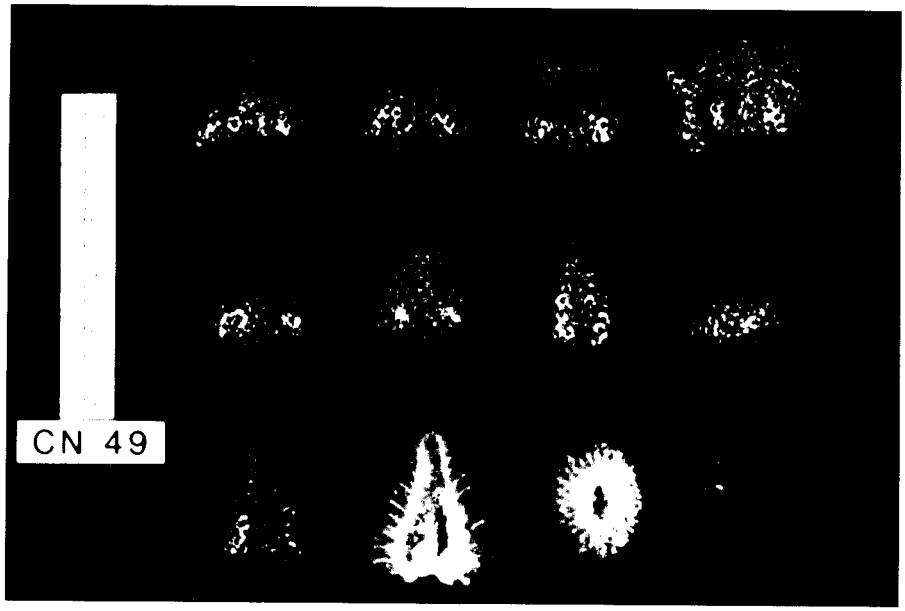
FIG. 3 shows representative early-season fruit with longitudinal and cross-sectional views.

'Seascape' commences fruiting about three months after planting, whether fresh dug or cold storage plants are used, regardless of planting time, provided that satisfactory growing conditions prevail. 'Seascape' is about as strongly day-neutral as 'Selva' or 'Muir' (U.S. Plant Pat. No. 6,558), considerably less strong than 'Irvine' (U.S. Plant Pat. No. pending), 'Hecker' (U.S. Plant Pat. No. 4,507) or 'Fern' (U.S. Plant Pat. No. 3,267). The difference is most evident in the nursery where only the mother and first daughter plants of 'Seascape' and 'Selva' and to a greater extent 'Muir' tend to flower and fruit strongly, whereas most of the daughter plants of 'Hecker' and 'Fern' and to a somewhat lesser extent 'Irvine' do so. Thus, ranking them in order of the tendency for plants to flower in the nursery, the order would be: 'Hecker' 'Fern', 'Irvine', 'Muir', 'Selva' and 'Seascape'. All are heterozygous for the day-neutral trait.

'Seascape' is of particular interest for winter and summer plantings in situations where 'Selva' is used successfully.

Plants and Foliage

Fruiting 'Seascape' plants are about as erect in growth habit as those of 'Selva'. Foliar characteristics from mid-summer 1988 central coast grown fruiting plants of 'Seascape' are compared with those of 'Irvine', 'Muir', 'Selva', and 'Fern' in Table 1.

TABLE 1

| | Seascape | Irvine | Muir | Selva | Fern |
|---|---|---|---|---|---|
| Munsell Color | 2.5GY43 | 7.5GY4/4 | 2.5GY4/3 | 7.5GY4/4 | 7.5GY4/4 |
| Shape (length/width) | 1.19 | 1.10 | 1.02 | 1.10 | 1.14 |
| Base angle of terminal leaflet | 48° | 53° | 60° | 55° | 50° |
| Size of terminal leaflets | 76 | 76 | 84 | 81 | 76 |
| Serrations of terminal leaflets | 11.4 | 9.4 | 11.2 | 11.2 | 12.0 |
| Petiolule length (MM) | 13 | 6.6 | 6.6 | 10.4 | 6.4 |
| Petiole length (MM) | 206 | 150 | 137 | 152 | 154 |

As shown above 'Seascape' leaves are about the same color as those of 'Muir', darker and less yellow than those of 'Irvine' or 'Selva' (Munsell Color System—Nickerson Color Fan). Terminal leaflets are somewhat similar in shape to those of 'Irvine' but a little longer and less round than those of 'Muir' as shown by the length/width measurement and half-blade terminal leaflet basal angle. 'Seascape' terminal leaflets are about the same size as those of 'Irvine', smaller than those of 'Muir' or 'Selva' as determined by extracting the square root of the length×width measurement. Terminal leaflet serration numbers are about the same as those for all the comparison cultivars except 'Irvine' which has less. The terminal leaflet petiolules of 'Seascape' are much longer than those of 'Muir' or 'Irvine' and somewhat longer than those of 'Selva'. 'Seascape' plants are larger than those of 'Selva', 'Muir' or 'Irvine' as indicated by petiole length. Bract leaflets are common on 'Seascape' petioles, similar to 'Muir' and 'Selva', in contrast to being rare on 'Irvine'. Runner production in nursery plants of 'Seascape' is quite good, about equal or better than for 'Selva' and 'Muir'.

Lysozymes in Leaf Extracts

'Seascape' has been classified for three enzyme systems by starch gel electrophoresis: A. Phosphoglucoisomerase (PGI); B. Leucine Amino Peptidase (LAP); and C. Phosphoglucomutase (PGM); and the results are compared with those for other day-neutral California cultivars in Table 2.

TABLE 2

| | Seascape & Fern | Irvine | Muir | Selva |
|---|---|---|---|---|
| PGI | A4 | A3 | A2 | H2 |
| LAP | B3 | B1 | B1 | B3 |
| PGM | C2 | C1 | C2 | C2 |
| | Hecker | Aptos & Brighton | Mrak | Yolo |
| PGI | A1 | A4 | A1 | A1 |
| LAP | B1 | B3 | B3 | B1 |
| PGM | C4 | C4 | C2 | C2 |

Thus, the 'Seascape' with the pattern (A4, B3 and C2) is identical to that of 'Fern' and short-day type 'Parker' (U.S. Plant Pat. No. 5,263) but can be distinguished from all other U.C. day-neutrals and short-day types. For the procedure, see: J. Amer. Soc. Hort. Sci. 106:687–1981.

Disease and Pest Reaction

'Seascape' is highly resistant to (tolerant of) the virus diseases common in California including "Mild Yellow Edge" and complexes containing it, moderately susceptible to common leaf spot (Ramularia), and is somewhat susceptible to the two-spotted mite.

Flowering, Fruiting, Fruit and Production Characteristics

'Seascape' is similar to California day-neutral cultivars 'Selva' and 'Muir' in that with a minimum of conditioning, it will flower and fruit anytime, effectively independent of day length. Flowers are borne on long, relatively thick peduncles, about as erect as those of 'Selva', less erect than those of 'Muir' and much less than those of 'Irvine'. The flowers have large petals averaging about six. The sepals are particularly large and attractive. 'Seascape' is self-fertile providing ample pollen throughout the season and pollination is generally good as relatively few malformed fruit form.

'Seascape' is capable of yielding about as much or more than other high-yielding day-neutral and short-day type cultivars and the fruit size is as large or larger on the average than that of 'Selva' (Tables 3, and 4). 'Seascape' plants are vigorous and have a little less of a chilling requirement than those of 'Selva' and can probably be planted earlier than 'Selva' with favorable results. Size varies considerably on 'Seascape' as the season advances or environmental conditions change but there is usually a high percentage of large fruit.

'Seascape' fruit shape is characteristically medium to occasionally long conic. The fruit of 'Seascape' is very firm, almost equal to 'Selva', 'Irvine' and 'Oso Grande' as measured by the penetrometer equipped with a "Hunter Force Gauge" and it stores and ships about as well as 'Selva' (Tables 3 and 4). The fruit is usually solid throughout.

'Seascape' fruit quality characteristics (ascorbic acid, soluble solids, titratable acid and color) are compared with those of 'Chandler', 'Douglas', 'Irvine', 'Oso Grande', and 'Selva' in Table 5, from plants grown under optimum conditions under the "hill" system in winter plantings at the University of California Strawberry Research Facility, Watsonville.

TABLE 3

Comparing the 1988 harvest of 'Seascape' over eight winter plantings and the 1989 harvest over four with those of appropriate cultivars at Watsonville. Means with the same letter not significantly different (5%).

| ITEM | TOT. YLD. G/PL | SIZE G/FR | FIRM PENET | AP SCORE | PERF* SCORE |
|---|---|---|---|---|---|
| 1988 Harvest | | | | | |
| Seascape | 1381 a | 24.6 a | 7.6 a | 3.8 a | 38.1 a |
| Fern | 1381 a | 20.0 c | 6.1 d | 3.1 cd | 31.4 cd |
| Irvine | 1309 a | 21.6 b | 7.8 a | 3.2 c | 33.1 bc |
| Selva | 1305 a | 22.3 b | 7.8 a | 3.3 d | 33.4 bc |
| Muir | 1090 bc | 21.6 b | 7.2 b | 3.1 cd | 29.9 de |
| Mrak | 1081 bc | 17.6 d | 6.5 c | 3.0 d | 29.9 e |
| Yolo | 938 c | 19.3 e | 7.1 b | 3.0 d | 27.2 e |
| 1989 Harvest | | | | | |
| Seascape | 1951 a | 26.3 a | 6.1 bc | 3.9 a | 40.4 b |
| Oso Grande | 1788 ab | 26.9 a | 6.6 a | 3.1 c | 38.4 bc |
| Irvine | 1710 ab | 21.8 ab | 6.5 abc | 2.9 de | 35.4 cd |
| Selva | 1528 b | 22.6 b | 6.6 ab | 3.1 cd | 34.3 d |
| Muir | 1523 b | 22.1 b | 6.0 c | 2.9 e | 33.2 d |
| Chandler | 1491 b | 25.6 a | 5.3 d | 3.4 b | 34.2 d |

Performance Score =

$$\frac{\text{TOTAL YLD}}{100} + \frac{\text{SIZE}}{3} + \text{FIRM} + 1.6\,(\text{AP SCORE})$$

TABLE 4

Comparing the 1987 harvest of 'Seascape' with that of 3 standard short-day type cultivars and 3 day-neutral cultivars in a summer planting made at Watsonville 3 Sept. 86.

| CULTIVAR | GPL BY 6 WKS ENDING 5/6 | 6/17 | 7/29 | 9/16 | TOT YLD G/PL |
|---|---|---|---|---|---|
| Chandler | 436 | 917 | 576 | 297 | 2227 |
| Oso Grande | 500 | 638 | 241 | 177 | 1559 |
| Pajaro | 423 | 621 | 300 | 202 | 1548 |
| Seascape | 655 | 625 | 590 | 291 | 2133 |
| Muir | 359 | 596 | 332 | 232 | 1521 |
| Selva | 417 | 522 | 266 | 219 | 1425 |
| Yolo | 451 | 311 | 166 | 105 | 1034 |

| CULTIVAR | TOT. YLD S.D. | SIZE G/FR | FIRM. PENET | AP. SCORE | PERF.* SCORE |
|---|---|---|---|---|---|
| Chandler | 255 | 16.5 | 4.7 | 3.1 | 37 |
| Oso Grande | 49 | 20.5 | 6.3 | 2.9 | 32 |
| Pajaro | 85 | 19.8 | 5.2 | 3.1 | 32 |
| Seascape | 7 | 19.1 | 5.1 | 3.5 | 38 |
| Muir | 36 | 22.3 | 5.4 | 3.1 | 33 |
| Selva | 287 | 22.1 | 6.0 | 3.1 | 32 |
| Yolo | 17 | 19.2 | 4.9 | 3.5 | 26 |

*Performance Score =

$$\frac{\text{TOTAL YLD}}{100} + \frac{\text{SIZE}}{3} + \text{FIRM} + 1.6\,(\text{AP SCORE})$$

TABLE 5

Fruit quality measurement and color, Watsonville 8 May 1989. Means with same letter not significantly different (5%)

| CULTIVAR | ASCORBIC ACID mg/100 g | SOL SOLIDS % | TIT. ACID % | COLOR |
|---|---|---|---|---|
| Chandler | 51 a | 7.3 a | 0.69 b | 5R4/12 |
| Seascape | 46 b | 7.0 ab | 0.74 b | 2.5R4/10 |
| Douglas | 43 bc | 6.8 b | 0.72 b | 6R4/12 |
| Irvine | 41 cd | 6.9 ab | 0.66 bc | 7R5/14 |
| Oso Grande | 40 cd | 5.7 c | 0.52 d | 7.5R4.5/11 |
| Selva | 33 e | 7.1 ab | 0.59 cd | 7R4/11 |

'Seascape' fruit averaged almost as high in ascorbic acid content as 'Chandler', as high as 'Douglas' and higher than 'Irvine', 'Oso Grande' and 'Selva' as measured by the Loeffler and Ponting method (1942, J. Indust. and Engin. Chem. 14:846). The fruit of 'Seascape' is relatively high in soluble solids and titratable acid (ibid). The fruit skin color is redder than that of all of the comparison cultivars inside and out. The finish is bright and attractive. The flesh color is about the same as that of the skin. The achenes are bright yellow to slightly reddish, positioned about flush to slightly exerted relative to the skin surface (ibid).

The flavor of 'Seascape' fruit is exceptional, better than that of 'Selva' or 'Irvine'. The fruit is recommended for fresh market and processing, for commercial planting and home gardening, particularly where 'off season' fruiting is desirable. The only cultivars that 'Seascape' resembles closely in performance are 'Selva' and 'Muir' and consequently it is of interest wherever they are currently grown.

We claim:

1. The new and distinct variety of strawberry plant herein described and illustrated and identified by the characteristics enumerated above.

* * * * *